(12) United States Patent
Fraatz et al.

(10) Patent No.: US 8,231,903 B2
(45) Date of Patent: Jul. 31, 2012

(54) CONTROLLED RELEASE SYSTEM

(75) Inventors: Kristine Fraatz, Leverkusen (DE); Dirk Mertin, Langenfeld (DE); Iris Heep, Cologne (DE)

(73) Assignee: Bayer Animal Health GmbH (DE)

( * ) Notice: Subject to any disclaimer, the term of this patent is extended or adjusted under 35 U.S.C. 154(b) by 906 days.

(21) Appl. No.: 11/243,293

(22) Filed: Sep. 12, 2005

(65) Prior Publication Data

US 2006/0034926 A1 Feb. 16, 2006
US 2009/0246277 A9 Oct. 1, 2009

Related U.S. Application Data

(63) Continuation of application No. PCT/EP2004/002318, filed on Mar. 6, 2004.

(30) Foreign Application Priority Data

Mar. 20, 2003 (DE) .................... 103 12 346

(51) Int. Cl.
*A61K 9/08* (2006.01)
*A61K 31/7024* (2006.01)
*A61K 31/496* (2006.01)
*A61K 31/4704* (2006.01)
*A61K 9/22* (2006.01)

(52) U.S. Cl. .............. 424/468; 514/53; 514/253.08; 514/312

(58) Field of Classification Search .................. None
See application file for complete search history.

(56) References Cited

U.S. PATENT DOCUMENTS

| | | | |
|---|---|---|---|
| 4,382,892 A | 5/1983 | Hayakawa et al. | |
| 4,472,405 A | 9/1984 | Stern | |
| 4,670,444 A | 6/1987 | Grohe et al. | |
| 4,704,459 A | 11/1987 | Todo et al. | |
| 4,730,000 A | 3/1988 | Chu | |
| 4,861,779 A | 8/1989 | Jefson et al. | |
| 5,736,152 A | 4/1998 | Dunn | |
| 5,744,153 A | 4/1998 | Yewey et al. | |
| 5,747,058 A * | 5/1998 | Tipton et al. | 424/423 |
| 5,968,542 A | 10/1999 | Tipton | |
| 6,190,689 B1 | 2/2001 | Hoffmann et al. | |
| 6,278,013 B1 | 8/2001 | Bartel et al. | |
| 6,323,213 B1 * | 11/2001 | Bartel et al. | 514/300 |
| 6,391,336 B1 * | 5/2002 | Royer | 424/468 |
| 6,667,058 B1 * | 12/2003 | Goede et al. | 424/473 |
| 6,992,065 B2 | 1/2006 | Okumu | |
| 7,128,927 B1 | 10/2006 | Dunn | |
| 7,318,931 B2 | 1/2008 | Okumu et al. | |
| 2005/0031650 A1 * | 2/2005 | Leroux et al. | 424/400 |
| 2006/0233841 A1 | 10/2006 | Brodbeck et al. | |

FOREIGN PATENT DOCUMENTS

| | | | |
|---|---|---|---|
| CA | 2314746 | | 2/2001 |
| WO | 0115734 A | | 3/2001 |
| WO | WO01/15734 | * | 3/2001 |
| WO | 2004032898 A | | 4/2004 |
| WO | WO2004/032898 | * | 4/2004 |

OTHER PUBLICATIONS

Matschke et. al. Review: Sustained-release injectables formed in situ and their potential use for veterinary producst. Journal of Controlled Release, vol. 85, Issues 1-3, Dec. 13, 2002 (available online Nov. 20, 2002), pp. 1-15.*
Schuster et al., "Flupertine: A Review of Its Neuroprotective and Behavioral Properties," CNS Drug Review, 1998, pp. 149-164, vol. 4, No. 2.
WHO Drug Information , vol. 15, No. 3-4, 2001.
Louis Mulligan, Enrofloxacin, Who Food Additives Series 34.
Gary Stein, "Review of the Bioavailability and Pharmacokinetics of Oral Norfloxacin," The American Journal of Medicine, Jun. 26, 1987, pp. 18-21, vol. 82, Issue 6, Supplement 2.
"Enrofloxacin," Petplace-Article.
PCT International Search Report dated Feb. 25, 2008, 7 pgs.

* cited by examiner

*Primary Examiner* — David J Blanchard
*Assistant Examiner* — Rachael E Bredefeld

(57) ABSTRACT

The invention relates to a system for controlled release of medicinally active substances, which comprises sucrose acetate isobutyrate (SAIB) and a further solvent.

2 Claims, No Drawings

CONTROLLED RELEASE SYSTEM

The invention relates to a system for controlled release of medicinally active substances which comprise sucrose acetate isobutyrate (SAIB) and a further solvent.

There has been extensive research in the area of the controlled release of active pharmaceutical ingredients by means of biodegradable systems. They have the advantage that they need not be removed from the body after discharging the active ingredient.

Biodegradable systems like those described in WO 96/39995 (and the corresponding U.S. Pat. Nos. 5,747,058 and 5,968,542) are simple and thus cost-effective. In these, a highly viscous liquid, preferably sucrose acetate isobutyrate (SAIB), serves as active ingredient carrier. However, because of the high viscosity, SAIB can ordinarily be administered parenterally only after dilution with a suitable solvent. Suitable solvents mentioned in the publications are ethanol, dimethyl sulphoxide, ethyl lactate, ethyl acetate, benzyl alcohol, triacetin, N-methylpyrrolidone, propylene carbonate and glycofurol. Solvents not previously proposed for this purpose are glycerol formal and Solketal (isopropylideneglycerol).

It has been found that glycerol formal and Solketal are miscible with SAIB and are outstandingly suitable for producing biodegradable pharmaceutical systems for controlled release of medicinally active substances. Addition of glycerol formal and/or Solketal improves the solvency for many active ingredients, especially for fluoroquinolones or analgesics such as, for example, flupirtine. It is thus possible by using glycerol formal and Solketal together with SAIB to obtain biodegradable pharmaceutical systems for slow release of active ingredient.

The invention therefore relates to:
A medicament comprising:
(a) a pharmaceutically active constituent
(b) sucrose acetate isobutyrate (SAIB)
(c) as solvent glycerol formal or isopropylideneglycerol or a mixture thereof.

The solvent is typically employed in a content of at least 5% by weight, preferably at least 10% by weight, particularly preferably at least 15% by weight, normally in the range from 5 to 80% by weight, preferably 10 to 70% by weight, in particular 15 to 60% by weight, where the data in % by weight are in each case based on the total weight of the formulation.

SAIB is usually employed in concentrations not exceeding 80% by weight, preferably not exceeding 75% by weight, for example in the range from 5 to 80% by weight, preferably 10 to 75% by weight, in each case based on the total weight of the formulation. Different release characteristics can be achieved by varying the SAIB concentration:

In one embodiment, the invention relates to depot formulations with sustained release; these normally contain from 50 to 80% by weight, preferably 60 to 75% by weight, of SAIB, based on the total weight of the formulation. Owing to the high SAIB content, it is inevitable that the solvent content in such formulations is less, and it is ordinarily less than 45% by weight, preferably less than 40% by weight, particularly preferably less than 30% by weight.

In a further embodiment, the invention relates to slow-release formulations with only slightly delayed release of the active ingredient; these normally contain from 10 to 50% by weight, preferably 20 to 40% by weight, of SAIB. Such slow-release formulations are, owing to the somewhat slower rise in level and a smaller burst of the active ingredient, often better tolerated than formulations with which the release of active ingredient is not delayed.

A suitable pharmaceutically active constituent is an active pharmaceutical ingredient or a combination of a plurality of active ingredients. The active pharmaceutical ingredients preferably employed in the medicaments according to the invention are fluoroquinolones or analgesics such as, for example, flupirtine. Fluoroquinolones are compounds disclosed inter alia in the following documents: U.S. Pat. No. 4,670,444 (Bayer AG), U.S. Pat. No. 4,472,405 (Riker Labs), U.S. Pat. No. 4,730,000 (Abbott), U.S. Pat. No. 4,861,779 (Pfizer), U.S. Pat. No. 4,382,892 (Daiichi), U.S. Pat. No. 4,704,459 (Toyama), and specific examples which may be mentioned are: benofloxacin, binfloxacin, cinoxacin, ciprofloxacin, danofloxacin, difloxacin, enoxacin, enrofloxacin, fleroxacin, ibafloxacin, levofloxacin, lomefloxacin, marbofloxacin, moxifloxacin, norfloxacin, ofloxacin, orbifloxacin, pefloxacin, pipemidic acid, temafloxacin, tosufloxacin, sarafloxacin, sparfloxacin.

A preferred group of fluoroquinolones are those of the formula (I) or (II):

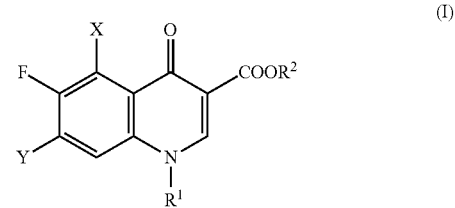

(I)

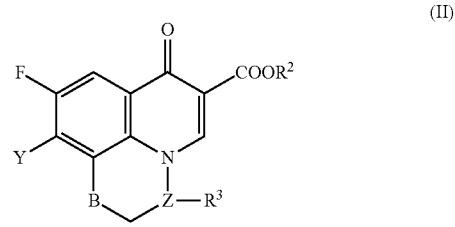

(II)

in which
X is hydrogen, halogen, $C_{1-4}$-alkyl, $C_{1-4}$-alkoxy, $NH_2$,
Y is radicals of the structures

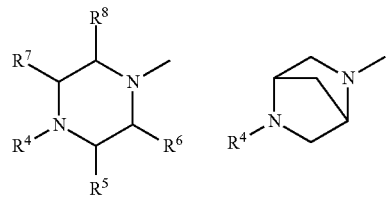

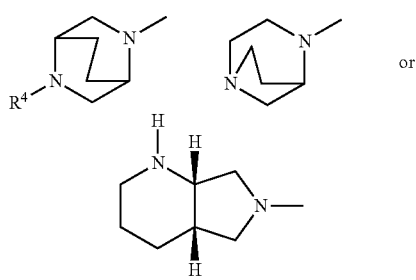

or in which

R⁴ is optionally hydroxy- or methoxy-substituted straight-chain or branched $C_1$-$C_4$-alkyl, cyclopropyl, acyl having 1 to 3 C atoms, R⁵ is hydrogen, methyl, phenyl, thienyl or pyridyl, R⁶ is hydrogen or $C_{1-4}$-alkyl, R⁷ is hydrogen or $C_{1-4}$-alkyl, R⁸ is hydrogen or $C_{1-4}$-alkyl, and R¹ is an alkyl radical having 1 to 3 carbon atoms, cyclopropyl, 2-fluoroethyl, methoxy, 4-fluorophenyl, 2,4-difluorophenyl or methylamino, R² is hydrogen or optionally methoxy- or 2-methoxyethoxy-substituted alkyl having 1 to 6 carbon atoms, and cyclohexyl, benzyl, 2-oxopropyl, phenacyl, ethoxycarbonylnethyl, pivaloyloxymethyl, R³ is hydrogen, methyl or ethyl, and A is nitrogen, =CH—, =C(halogen)-, =C(OCH₃)—, =C(CH₃)— or =C(CN), B is oxygen, optionally methyl- or phenyl-substituted =NH or =CH₂, Z is =CH— or =N—, and the pharmaceutically usable salts and hydrates thereof.

The compounds of the formulae (I) and (II) may be in the form of their racemates or in enantiomeric forms.

Preference is given to compounds of the formula (I) in which

A is =CH— or =C—CN,

R¹ is optionally halogen-substituted $C_1$-$C_3$-alkyl or cyclopropyl,

R² is hydrogen or $C_{1-4}$-alkyl,

Y is radicals of the structures

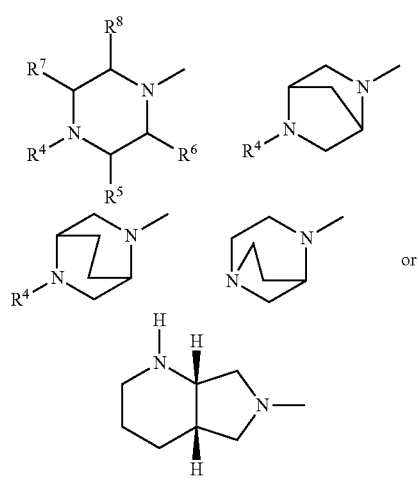

in which

R⁴ is optionally hydroxy-substituted straight-chain or branched $C_1$-$C_3$-alkyl, oxoalkyl having 1 to 4 C atoms, R⁵ is hydrogen, methyl or phenyl, R⁷ is hydrogen or methyl, and the pharmaceutically usable hydrates and salts thereof.

Particular preference is given to compounds of the formula (I), in which

A is =CH— or =C—CN,

R¹ is cyclopropyl,

R² is hydrogen, methyl or ethyl,

Y is radicals of the structures

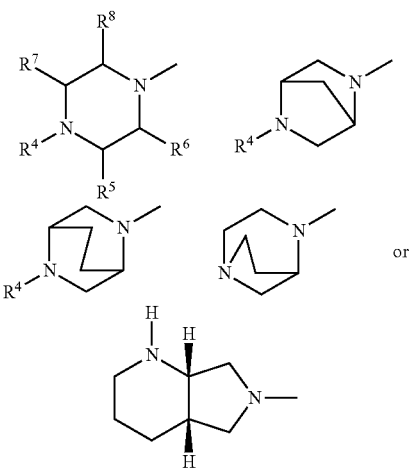

in which

R⁴ is methyl, optionally hydroxy-substituted ethyl,

R⁵ is hydrogen or methyl,

R⁷ is hydrogen or methyl, and the pharmaceutically usable salts and hydrates thereof.

Suitable salts are pharmaceutically usable acid addition salts and basic salts.

Examples of pharmaceutically usable salts are the salts of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid. The compounds according to the invention are also able to bind to acetic or basic ion exchangers. Pharmaceutically usable basic salts which may be mentioned are the alkali metal salts, for example the sodium or potassium salts, the alkaline earth metal salts, for example the magnesium or calcium salts; the zinc salts, the silver salts and the guanidinium salts.

Hydrates mean both the hydrates of the fluoroquinolones themselves and the hydrates of the salts thereof.

Particularly preferred fluoroquinolones which may be mentioned are the compounds described in WO 97/31001, in particular 8-cyano-1-cyclopropyl-7-(1S,6S)-2,8-diazabicyclo[4.3.0]nonan-8-yl)-6-fluoro-1,4-dihydro-4-oxo-3-quinolinecarboxylic acid (pradofloxacin) having the formula

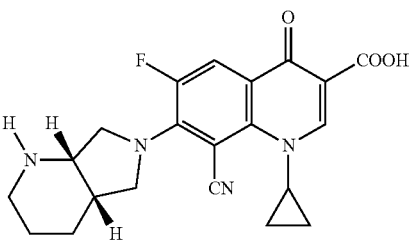

also particularly preferably employed is enrofloxacin:

1-cyclopropyl-7-(4-ethyl-1-piperazinyl)-6-fluoro-1,4-dihydro-4-oxo-3-quinolinecarboxylic acid

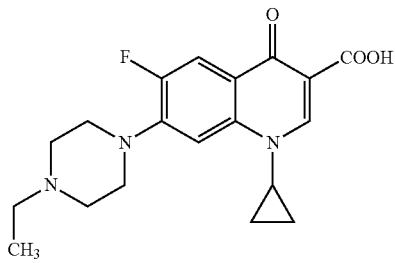

also preferred as active ingredient is the analgesic flupirtine of the following formula:

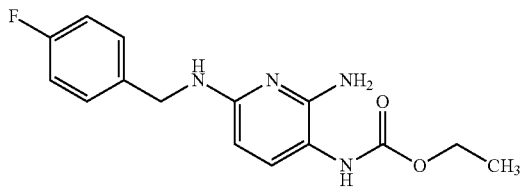

flupirtine can likewise be employed in the form of its pharmaceutically usable salts, preferably salts with acids such as, for example, the hydrochloride or the maleate.

The pharmaceutically active constituent is normally employed in a content of from 0.1 to 20% by weight, preferably from 0.1 to 15% by weight, in particular from 1 to 15% by weight, based on the total weight of the medicament. Relatively high concentrations of from 1 to 15% by weight, preferably 5 to 15% by weight, based on the total weight of the medicament, are usual for agricultural livestock. Somewhat lower concentrations in the range from 0.1 to 12% by weight, preferably 1 to 6% by weight, based on the total weight of the medicament, are usual for pets such as, for example, dogs and cats.

The medicaments may also contain cosolvents which reduce the viscosity of the formulations. These are normally employed in contents of from 1 to 10% by weight, preferably from 3 to 8% by weight. Examples of cosolvents which may be mentioned are: pharmaceutically acceptable alcohols, dimethyl sulphoxide, ethyl lactate, ethyl acetate, triacetin, N-methylpyrrolidone, propylene carbonate, glycofurol, dimethylacetamide, 2-pyrrolidone, glycerol and polyethylene glycols. Particularly suitable as cosolvents are pharmaceutically acceptable alcohols such as, for example, ethanol, benzyl alcohol or n-butanol. Mixtures of the aforementioned solvents can also be employed as cosolvent.

The medicaments according to the invention are distinguished by good solubility properties for active ingredients, so that in many cases adequate active ingredient concentrations in the medicament are achieved even with the neutral form of the active ingredient (e.g. zwitterionic form in the case of quinolone antibiotics). It is thus possible to produce, depending on the active ingredient and its isoelectric point, compositions whose pH is advantageously in the vicinity of neutrality, preferably at pH 6 to 8. Extreme pH values are normally avoided in medicaments, e.g. in formulations for injection, because the tolerability and stability are ordinarily better in the vicinity of pH 7. Formulations according to the invention of pradofloxacin in which the pradofloxacin is soluble to a sufficient extent at pH 7.4 may be mentioned as example. The pH is adjusted by adding pharmaceutically acceptable acids or bases, e.g. as aqueous solution, to the compositions according to the invention.

The medicaments according to the invention can be produced by mixing the solvent with SAIB, and dissolving the active ingredient in the mixture. Cosolvents, and further constituents, may have previously been added to the solvent or may be admixed later.

An alternative possibility is first to dissolve the active ingredient in the solvent, then further cosolvents are added where appropriate to the solution, and finally the SAIB is added.

The pharmaceutical preparations according to the invention are generally suitable for the use in humans and animals. They are preferably employed in livestock management and livestock breeding among agricultural and breeding livestock, zoo, laboratory and experimental animals and pets.

The agricultural and breeding livestock include mammals such as, for example, cattle, horses, sheep, pigs, goats, camels, water buffalo, donkeys, rabbits, fallow deer, reindeer, fur-bearing animals such as, for example, mink, chinchilla, raccoon, and birds such as, for example, chickens, geese, turkeys, ducks, pigeons and bird species for keeping at home and in zoos.

The laboratory and experimental animals include mice, rats, guinea pigs, golden hamsters, dogs and cats.

Pets include rabbits, hamsters, guinea pigs, mice, horses, reptiles, appropriate bird species, dogs and cats.

Mention may also be made of fish, specifically used for farming, breeding, aquarium and ornamental fish of all ages which live in fresh and salt water.

The preparations according to the invention are preferably employed for pets such as horses, cats and dogs. They are particularly suitable for use in cats and dogs.

Examples of preferred agricultural livestock, cattle, sheep, pigs and fowl.

Both prophylactic and therapeutic use are possible.

The formulations described herein can be supplied to the target organism (human or animal) in various ways. They can be administered for example parenterally (e.g. subcutaneously, intramuscularly, intraperitoneally), dermally, orally, rectally, vaginally or nasally, with preference for parenteral administration.

The formulations are preferably given as solutions, paste, suspension or emulsion. On injection of a solution, the small amount of solvent diffuses into the surrounding tissue or the interstitial fluid and leaves behind a highly viscous depot from which there is delayed release of active ingredient. The rate of breakdown of the depot can be slowed down through addition of an additive such as, for example, of a polymer.

Examples of biodegradable polymers or oligomers which may be mentioned are: poly(lactides), poly(lactide-coglycolides), poly(glycolides), poly(caprolactones), polyamides, polyanhydrides, polyamino acids, polyorthoesters, polycyanacrylates, poly(phosphazines), poly(phosphoric esters), polyesteramides, polydioxanones, polyacetals, polyketals, polycarbonates, polyorthocarbonates, degradable polyurethanes, polyhydroxybutyrates, polyhydroxyvalerates, polyalkylene oxalates, polyalkylene succinates, poly(malic acid), chitin, chitosan, and copolymers, terpolymers, oxidized cellulose or combinations or mixtures of the aforementioned materials. Examples of poly(alpha-hydroxy acids) are, inter alia: poly(glycolic acid), poly(DL-lactic acid) and poly(L-lactic acid) and copolymers thereof. Examples of polylactones are, inter alia: poly(epsilon-caprolactone), poly(delta-valerolactone) and poly(gamma-butyrolactone).

Examples of non-biodegradable polymers or oligomers which may be mentioned are: poly-acrylates, ethylene/vinyl acetate polymers, cellulose and cellulose derivatives, acyl-substituted cellulose acetates and derivatives, non-degradable polyurethanes, polystyrenes, polyvinyl chloride, polyvinyl fluoride, polyvinylimidazole, chlorosulphonated polyolefins and polyethylene oxide; preferred examples thereof are: polyethylene, polyvinylpyrrolidone, ethylene/vinyl acetate, polyethylene glycol, cellulose acetate butyrate ("CAB") and cellulose acetate propionate ("CAP").

Depending on the nature of the formulation and form of administration, the medicaments according to the invention may comprise further conventional, pharmaceutically acceptable additives and excipients. Examples which may be mentioned are

- preservatives such as, for example, carboxylic acids (sorbic acid, propionic acid, benzoic acid, lactic acid), phenols (cresols, p-hydroxybenzoic esters such as methylparaben, propylparaben etc.), aliphatic alcohols (benzyl alcohol, ethanol, butanol etc.), quaternary ammonium compounds (benzalkonium chloride, cetylpyridinium chloride)
- Antioxidants such as, for example, sulphites (Na sulphite, Na metabisulphite), organic sulphides (cystine, cysteine, cysteamine, methionine, thioglycerol, thioglycolic acid, thiolactic acid), phenols (tocopherols, as well as vitamin E and vitamin E-TPGS (d-alpha-tocopheryl polyethylene glycol 1000 succinate), butylated hydroxyanisole, butylated hydroxytoluene, octyl gallate and dodecyl gallate), organic acids (ascorbic acid, citric acid, tartaric acid, lactic acid) and salts and esters thereof.
- wetting agents such as, for example, fatty acid salts, fatty alkyl sulphates, fatty alkyl-sulphonates, linear alkylbenzenesulphonates, fatty alkyl polyethylene glycol ether sulphates, fatty alkyl polyethylene glycol ethers, alkylphenol polyethylene glycol ethers, alkyl polyglycosides, fatty acid N-methylglucamides, polysorbates, sorbitan fatty acid esters and poloxamers.
- pharmaceutically acceptable colours such as, for example, iron oxide, carotenoids, etc.

The use of SAIB in combination with the said solvents results in medicaments having good solubility and stability of the active ingredient. The medicament according to the invention is furthermore distinguished by good tolerability, especially after parenteral administration. It is moreover possible to influence the release of active ingredient.

EXAMPLES

The formulations of the following examples were produced by mixing the solvents or cosolvents with SAIB, and dissolving the various ingredients (pradofloxacin, enrofloxacin, flupirtine) in the mixtures. The pH of the solutions can be adjusted by adding acids or bases. Clear solutions of medium viscosity result. The solutions are sterilized by filtration and transferred into suitable containers. (Percentage data in per cent by weight, based on the total weight of the finished product).

Example 1

40% SAIB
3% pradofloxacin
3% n-butanol
5% ethanol
1.7% 1N HCl
ad 100% glycerol formal 3 g of pradofloxacin are dissolved in a mixture of 3 g of n-butanol, 5 g of ethanol, 40 g of SAIB, and 47.3 g of glycerol formal. 1.7 g of 1N hydrochloric acid are added to the solution to adjust the pH to about 7.4.

Example 2

40% SAIB
1% enrofloxacin
5% ethanol
ad 100% Solketal 1 g of enrofloxacin are dissolved in a mixture of 40 g of SAIB, 5 g of ethanol and 54 g of Solketal.

Example 3

30% SAIB
1.5% pradofloxacin
3% n-butanol
ad 100% Solketal 1.5 g of pradofloxacin are dissolved in a mixture of 3 g of n-butanol, 30 g of SAIB and 65.5 g of Solketal.

Example 4

50% SAIB
5% flupirtine
5% ethanol
ad 100% glycerol formal 5 g of flupirtine are dissolved in a mixture of 5 g of ethanol, 50 g of SAIB and 40 g of glycerol formal.

Example 5

10% SAIB
6% pradofloxacin
5% ethanol
2.4% 1N HCl
ad 100% glycerol formal 6 g of pradofloxacin are dissolved in a mixture of 5 g of ethanol, 10 g of SAIB and 76.6 g of glycerol formal. 2.4 g of 1N hydrochloric acid are added to the solution to adjust the pH to about 7.4.

The invention claimed is:

1. An injectable medicament comprising:
   a. Pradofloxacin, wherein the pradofloxacin is in an amount of 5 to 15% by weight based on the total weight of the medicament;
   b. sucrose acetate isobutyrate (SAIB), wherein the SAIB is in an amount of 10 to 75% by weight based on the total weight of the medicament;
   c. a solvent selected from the group consisting of glycerol formal, isopropylideneglycerol, and a mixture thereof, and
   d. a cosolvent, wherein the cosolvent is selected from the group consisting of ethanol, n-butanol, and benzyl alcohol and is in an amount of 1 to 10% by weight based on the total weight of the medicament.

2. The medicament according to claim 1, wherein the solvent is glycerol formal.

* * * * *